US00PP32227P2

(12) United States Plant Patent
Hansen

(10) Patent No.: US PP32,227 P2
(45) Date of Patent: Sep. 22, 2020

(54) ***DIANTHUS* PLANT NAMED 'KISS AND TELL'**

(50) Latin Name: ***Dianthus* hybrid**
Varietal Denomination: Kiss and Tell

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/873,018

(22) Filed: Jan. 15, 2020

(51) Int. Cl.
*A01H 5/02* (2018.01)
*A01H 6/30* (2018.01)

(52) U.S. Cl.
USPC ..... Plt./272
CPC ..... *A01H 6/305* (2018.05)

(58) Field of Classification Search
USPC ..... Plt./272
CPC ..... A01H 5/0233
See application file for complete search history.

*Primary Examiner* — Kent L Bell

(57) ABSTRACT

A new and unique plant cultivar of perennial carnation or pinks, *Dianthus* plant named 'Kiss and Tell' with numerous, medium-sized, semi-double, lightly-sweet, spicy, fragrant flowers producing a rounded semi-spherical face. The numerous stems cover top to bottom of clump on well-branched stems having up to 3 flowers per stem. Petals have small serrations in the margin and are colored faint pink with a broad dark-red band near the base of the petal limb. The habit is compact with dense blue-green foliage.

1 Drawing Sheet

Botanical denomination: *Dianthus* hybrid.
Cultivar designation: 'Kiss and Tell'.

STATEMENT REGARDING PRIOR DISCLOSURES UNDER 37 CFR 1.77(b)(6)

The first non-enabling disclosure of the claimed plant was made by Walters Gardens, Inc. on Feb. 1, 2019 in the form of a website brief description and photograph, followed by a short description and photograph in the "Walters Gardens 19-20 Catalog" by Walters Gardens, Inc. The first sales of the claimed plant was on Jul. 8, 2019 by Walters Gardens, Inc. Walters Gardens, Inc. obtained the new plant and information about the new plant directly from the inventor. No plants of *Dianthus* 'Kiss and Tell' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of carnation or pinks from the genus *Dianthus* and given the cultivar name 'Kiss and Tell'. The new plant was the result of an intentional cross on Nov. 19, 2014 under the direction of the inventor between the unnamed, proprietary hybrid known by the breeder code 12-351-2 as the female or seed parent and the unnamed, proprietary hybrid known by the breeder code 12-251-1 as the male or pollen parent. The cross was harvested in February and sown in the spring of 2015. The new hybrid was first selected from trials at a wholesale perennial nursery in Zeeland, Mich. during the summer of 2015 as a single seedling clone and given the breeder code number 14-49-1 later in the evaluation processes. *Dianthus* 'Kiss and Tell' has been asexually propagated at the same nursery in Zeeland, Mich. since 2016 using traditional shoot tip cutting procedures and later sterile shoot-tip tissue culture and found to reproduce plants that are identical and exhibit all the characteristics of the original plant.

SUMMARY OF THE INVENTION

*Dianthus* 'Kiss and Tell' has not been evaluated under all possible environmental conditions. The phenotype may vary with variations in environment including: growing temperature, available sunlight, nutrients, water, etc. without a change in the genotype of the plant.

Plants nor photographs of the two parents were not maintained so comparison is not possible. The new plant can be compared with the great grandparents: 'Double North' (not patented), 'Coconut Punch' U.S. Plant Pat. No. 21,876. 'Double North' has fragrant, double, white flowers with no reddish bar, the stem strength is not as strong and rigid and the petals are more deeply toothed in the apex than the new plant. The flower of 'Coconut Punch' has a slightly thinner dark red band near the base of the limb, but also has a dark red margin and slightly more petals per flower. The distal portion of the 'Coconut Punch' flower is also whiter. The new plant can also be compared with 'Appleblossom Burst' U.S. Plant Pat. No.31,454. 'Appleblossom Burst' has a greater color change in the flowers starting light pink and becoming faint pink in the distal portion, and the petal limb base has a much narrower and light red band.

*Dianthus* 'Kiss and Tell' is distinct from all other *Dianthus* known to the applicant in the following combined traits:

1. Semi-double flowers opening up with a rounded semi-spherical face.
2. Petals open a faint pink with a broad darker red bar in the bottom half of the petal limb.
3. Distal petal color lightens with age to near white;

4. Petal margin finely irregularly toothed;
5. Multiple flowers per stiff, upright peduncle;
6. Medium flower size producing a lightly-sweet spicy fragrance;
7. Compact habit and dense blue-green foliage.

BRIEF DESCRIPTION OF THE DRAWINGS

The photographs of 'Kiss and Tell' are of a two-year-old plant grown in full-sun trial garden in Zeeland, Mich. showing the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
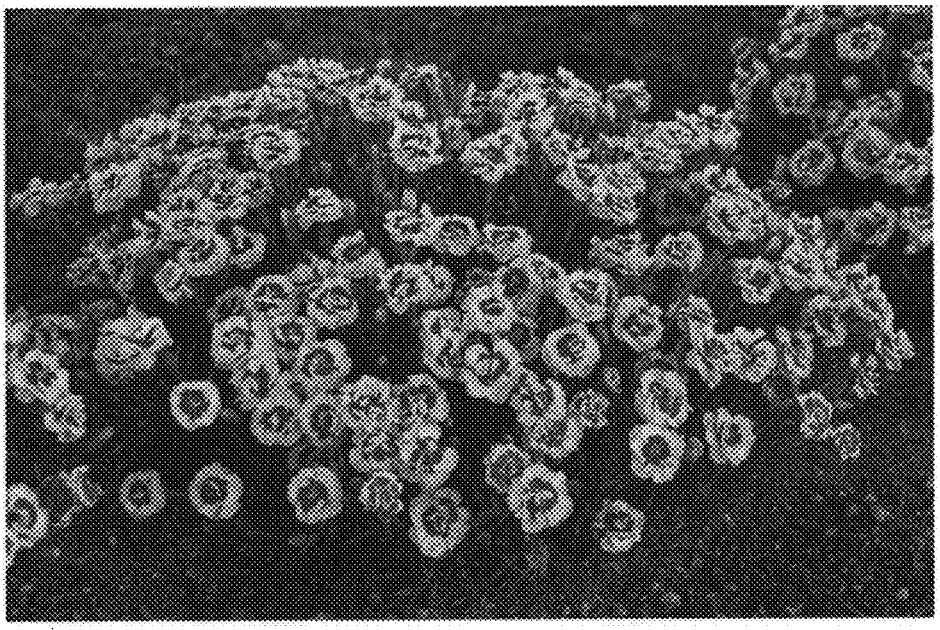
FIG. 1 shows the habit of the plant in mid-season flowering.
Figure 2:
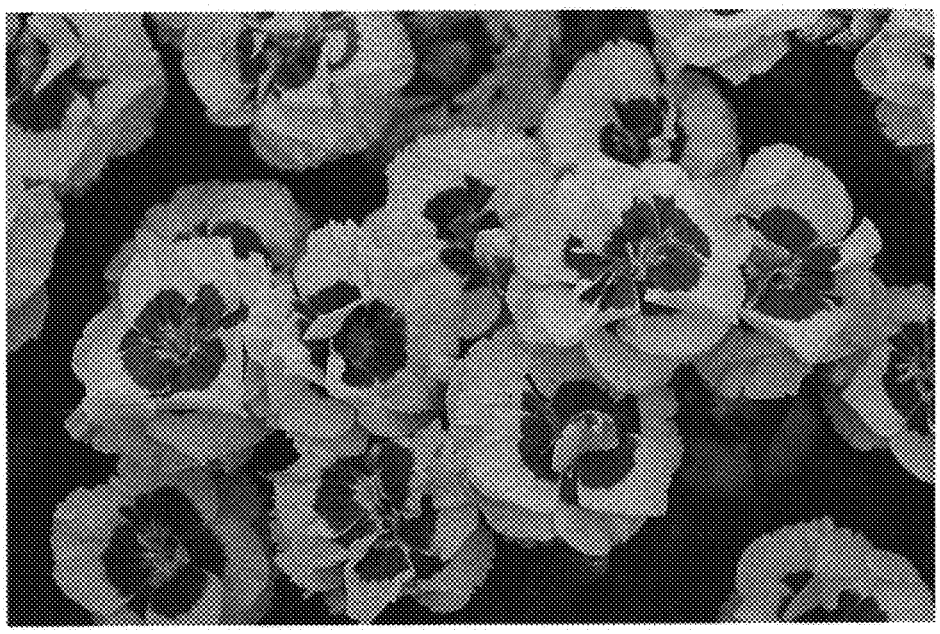
FIG. 2 shows a close-up of the flowers and bud.

The following detailed description of the new plant is based on observations of two-year-old plants in a partially shaded greenhouse and also full-sun trial garden at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: The female or seed parent is 12-351-02; the male or pollen parent is 12-251-1;

Plant habit: Caespitose, herbaceous, evergreen, winter-hardy perennial; stems and peduncles highly branched, mostly erect stems; height of foliage about 15.0 cm and about 52.0 cm across; height in flower is about 26.0 cm;

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, glaucous both adaxial and abaxial; margin entire to microscopically serrulate; acute narrowly apex; base truncate, decurrent, clasping; no fragrance detected.

*Leaf dimensions*.—To about 9.5 cm long and about 6.0 mm wide, average about 7.2 cm long and 4.5 mm wide.

*Leaf color*.—Young expanding leaves adaxial and abaxial nearest RHS 139C; mature adaxial and abaxial blend between RHS N138B and RHS N138A.

*Venation*.—Not pronounced; obscurely pinnate, coloration same as that of leaf top and bottom.

Stems: About 92 per plant; upright; cylindrical, glabrous, glaucous; hollow; branching in upper nodes;

*Stem size*.—Hollow; terete; about 21.0 cm long to peduncle and about 3.0 mm wide at base.

*Stem color*.—Blend between RHS 189A, RHS 189B and RHS 122A.

*Branching*.—Numerous; typically alternate from lower nodes; about 5 per main stem and about 200 per plant; branch size average about 3.5 cm long and 1.0 mm diameter at time of initial flowering.

*Nodes*.—Slightly swollen; about nine per stem; about 3.5 mm across; color nearest RHS 142D.

*Internodes*.—About 9 per stem before peduncle; average about 2.3 cm apart depending on growing temperature, shorter in cooler conditions.

Inflorescence:

*Type*.—Terminal, cymose; perfect; salverform; actinomophic; semi-double.

*Attitude*.—Upright to slightly outward around perimeter of plant.

*Dimension*.—About 4.0 cm across and extending about 3.2 cm above base of calyx tube and 8.0 mm wide at apex of calyx.

*Flowers per stem*.—Up to 3, average 2.

*Pedicel*.—Glaucous, glabrous, cylindrical, stiff; primarily upright.

*Pedicel size*.—Terminal flower to about 5.5 mm long and about 2.5 mm diameter; other flowers average about 2.0 mm long and 1.0 mm diameter.

*Pedicel color*.—Blend between RHS 189A, RHS 189B and RHS 122A.

*Flower bud*.—Cylindrical; glabrous; glaucous; attenuate base and truncate flat apex; about 31.0 mm long and 8.0 mm across at distal fusion point of sepals.

*Flower bud color*.—Exposed petals between RHS 73B and RHS 70D, calyx distally nearest RHS 138A and proximally nearest RHS N144D.

*Flower period*.—Beginning late spring and continuing for about three weeks.

*Flower fragrance*.—Light, sweet spicy, clove-like.

*Flower lasting quality*.—Individually about seven to ten days on or cut from plant.

*Petals*.—Glabrous except adaxial base of blade micropuberulent; up to about 21 per flower, average about 18.3; consisting of a rounded blade or limb and a claw; limb and claw combined are flabellate; limb apex rounded and margin irregularly crenate to dentate with indentations about 1.0 mm deep and average 2.0 mm wide; limb bent outwardly in distal 20.0 mm to nearly a ninety degree angle creating a flat rounded face; with single dark red band about 10 mm long at base of blade; persistent.

*Petal dimensions*.—Limb to about 20.0 mm across, average about 17.0 mm across; claw about 18 mm long, tapering to attenuate base of about 1.0 mm across; whole petal to about 38.0 mm long, average about 30.5 mm long.

*Petal color*.—Young adaxial claw nearest RHS 145B, adaxial limb base nearest RHS 71A and distal 10 mm lighter than RHS N66D; young abaxial claw nearest RHS 145B, young abaxial limb base nearest RHS 76D, distal blade lighter than RHS N66D; mature adaxial claw nearest RHS 145D, mature adaxial limb basal 10 mm between RHS 70A and RHS N79C and distal limb nearest RHS 69B, mature abaxial claw nearest RHS 145D, mature abaxial limb base nearest RHS 155B with undertone of between RHS 70A and RHS N79C, distally nearest RHS 69B.

*Calyx*.—Terete to campanulate; to about 22.0 mm long and 8.0 mm diameter at apex.

*Sepals*.—Five; lanceolate; acute apex and fused in basal 17.0 mm forming five-toothed calyx tube; glabrous; glaucous abaxial; margins entire to microciliolate.

*Sepal size*.—Individually about 22.0 mm long and about 5.0 mm across at distal fusion.

*Sepal color*.—Adaxial 0.5 mm wide margin translucent to nearest RHS 158D, distally nearest RHS 138B, proximally nearest RHS 145C; abaxial distally nearest RHS 138A with 0.5 mm wide translucent margin nearest RHS 158D, proximally nearest RHS N144D.

*Peduncle*.—Glabrous; glaucous; hollow, cylindrical; stiff; about 7.0 cm long and about 2.5 mm diameter at base; attitude mostly upright.

*Peduncle color*.—Blend between RHS 189A, RHS 189B and RHS 122A.

*Epicalyx*.—Two pairs subtending each flower; opposite, glaucous, glabrous; sessile, margin entire; outer pair oblanceolate with narrowly acute apex and truncate base, about 18.0 mm long and 6.0 mm wide, adaxial and abaxial color blend between RHS N138B and RHS N138A with 0.5 mm wide translucent margin in proximal one-third of nearest RHS 158C; inner pair deltoid with acute apex and truncate base, about 14.0 mm long and 10.0 mm across, color adaxial and abaxial distal one-third nearest RHS 139A, adaxial proximal two-thirds nearest RHS 146D and abaxial proximal two-thirds nearest RHS 144A, adaxial and abaxial translucent margin of about 1.5 mm wide in proximal one-half and about 0.5 mm wide in distal one-half nearest RHS 158C.

*Androecium*.—Typically ten; not fully developed.

*Filaments*.—Applanate along ovary; straight; to about 17.0 mm long and 0.5 mm diameter; color nearest RHS NN155A. Anther: rudimentary; basifixed; about 2.0 mm long and 0.7 mm wide and 0.2 mm thick; color nearest RHS NN155A. Pollen: not observed.

*Gynoecium*.—Single; to about 30.0 mm long. Style: bifurcate just above ovary; to 18.0 mm long naturally and arcuate 360° in distal 8.0 mm; color nearest RHS NN155B. Stigma: slightly flattened abaxial to adaxial; pubescent on adaxial surface distally; about 15.0 mm long and 1.0 mm wide; color nearest RHS N155D. Ovary: superior; oblong ellipsoidal to spindle-shaped with rounded apex and base; about 12.0 mm long and 5.0 mm wide in middle; color distally nearest RHS 146D, proximally between RHS 145C and RHS 145D.

Fruit and seed: Not observed;

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Kiss and Tell' essentially as herein described and illustrated.

* * * * *